United States Patent
Cheung et al.

(10) Patent No.: US 6,696,056 B1
(45) Date of Patent: Feb. 24, 2004

(54) PHARMACEUTICAL COMPOSITIONS OF ERYTHROPOIETIN

(75) Inventors: Wing K. Cheung, Warren, NJ (US); Jaya Natarajan, Hillsborough, NJ (US); Marilyn Sanders, Raritan, NJ (US); Els Vercammen, Dietlikon (CH); Selima Begum, Edison, NJ (US); Basant Sharma, Bridgewater, NJ (US)

(73) Assignee: Ortho McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/545,479

(22) Filed: Apr. 7, 2000

Related U.S. Application Data
(60) Provisional application No. 60/128,596, filed on Apr. 9, 1999.

(51) Int. Cl.$^7$ .......................... A61K 38/19; A61K 38/22
(52) U.S. Cl. ............................ 424/85.1; 514/8; 514/21
(58) Field of Search ............................ 424/85.1; 514/8, 514/12, 21; 530/351, 395, 397

(56) References Cited

U.S. PATENT DOCUMENTS

| | | | | |
|---|---|---|---|---|
| 4,806,524 A | * | 2/1989 | Kawaguchi et al. | 514/8 |
| 4,879,272 A | * | 11/1989 | Shimoda et al. | 514/8 |
| 4,992,419 A | | 2/1991 | Woog et al. | 514/8 |
| 5,376,632 A | | 12/1994 | Konings et al. | 514/8 |
| 5,661,125 A | | 8/1997 | Strickland et al. | 514/8 |
| 5,935,566 A | | 8/1999 | Yuen | 424/85.7 |
| 6,120,761 A | * | 9/2000 | Yamazaki et al. | 424/85.1 |

FOREIGN PATENT DOCUMENTS

| | | |
|---|---|---|
| EP | 0 366 277 A2 | 5/1990 |
| RU | 2 122 403 C1 | 11/1998 |
| WO | WO97-40850 | 11/1997 |
| WO | WO97-48411 | 12/1997 |

OTHER PUBLICATIONS

Ateshkadi, Arasb, PharmD; Johnson, Curtis A., PharmD; Oxton, Lisa L., MT(ASCP); Hammond, Timothy G., MD; Bohenek, Wayne S., PharmD; Zimmerman, Stephen W., MD. Pharmacokinetics of Intraperitoneal, Intravenous, and Subcutaneous Recombinant Human Erythropoietin in Patients on Continuous Ambulatory Peritoneal Dialysis. American Journal of Kidney Diseases, vol. 21, No. 6, Jun., pp. 635–642, 1993.

Breymann, Christian; Bauer, Christian; Major, Attila; Zimmerman, Roland; Gautschi, Kurt; Huch, Albert; Huch, Renate. Optimal timing of repeated rh–erythropoietin administration improves its effectiveness in stimulating erythropoiesis in healthy volunteers. British Journal of Haemotology, 92, 292–301, 1996.

Egrie, J.C.; Strickland, T.W. Lane, J.; Aoki, K.; Cohen, A.M.; Smalling, R.; Trail, G., Lin, F.K.; Browne, J.K.; Hines, D.K. Characterization and Biological Effects of Recombinant Human Erythropoietin. Immunobiol. vol. 172, pp. 213–224 (1986).

Faulds, Diana; Sorkin, Eugene M. Epoetin (Recombinant Human Erythropoietin) A Review of its Pharmacodynamic and Pharmacokinetic Properties and Therapeutic Potential in Anaemia and the Stimulation of Eryhropoiesis. Drugs 38 (6):863–899, 1989.

(List continued on next page.)

Primary Examiner—Jeffrey E. Russel
(74) Attorney, Agent, or Firm—Woodcock Washburn LLP

(57) ABSTRACT

The present invention provides aqueous pharmaceutical formulations of erythropoietin that are free of human serum blood products, stabilized with a quantity of an amino acid and a sorbitan mono-9-octadecenoate poly(oxy-1,2-ethanediyl) derivative. The present invention also provides aqueous stable, preserved pharmaceutical formulations of erythropoietin that contain an antimicrobial quantity of cresol and a quantity of an amino acid.

55 Claims, 4 Drawing Sheets

OTHER PUBLICATIONS

Frenken, L.A.M., MD; van Lier, H.J.J., MSc; Jordans, J.G.M., MD, PhD; Leunissen, K.M.L., MD, PhD; van Leusen, R., MD, PhD; Verstappen, V.M.C., MD; Koene, R.A.P., MD, PhD. Identification of the Component Part in an Epoietin Alfa Preparation That Causes Pain After Subcutaneous Injection. American Journal of Kidney Diseases, vol. 22, No. 4, (Oct):pp 553–556, 1993.

Granolleras, C.; Leskopf, W.; Shaldon, S.; Fourcade, J. Experience of pain after subcutaneous administration of different preparations of recombinant human erythropoietin: a randomized, double–blind crossover study. Clinical Nephrology, vol. 36, No. 6—(294–298), 1991.

Halstenson, Charles E., PharmD; Macres, Mark, MS; Katz, Stephen A., PhD; Schneiders, James R., MS; Watanabe, Masakazu; Sobota, Joseph T., MD; Abraham, Paul A., MD. Comparative pharmacokinetics and pharmacodynamics of epoetin alfa and epoetin beta. Clin Pharmacol Ther, 50:702–12, 1991.

Jacobs, Kenneth; Shoemaker, Charles; Rudersdorf, Richard; Neill, Suzanne D.; Kaufman, Randal J.; Mufson, Allan, Seehra, Jasbir; Jones, Simon S.; Hewick, Rodney; Fritsch, Edward F.; Kawakita, Makoto; Shimizu, Tomoe; Miyake, Takaji. Isolation and characterization of genomic and cDNA clones of human erythropoietin. Letters to Nature, vol. 313, Feb. 28, 1985.

Jelkmann, Wolfgang. Erythropoietin: Structure, Control of Production, and Function. Physiological Reviews, vol. 72, No. 2, Apr., 1992.

Koury, Stephen T.; Bondurant, Maurice C.; Koury, Mark J. Localization of Eryhropoietin Synthesizing Cells in Murine Kidneys By In Situ Hybridization. Concise Report, Blood, vol. 71, No. 2, (Feb.): pp 524–527, 1988.

Lin, Fu–Kuen; Suggs, Sidney: Lin, Chi–Hwei; Browne, Jeffrey K.; Smalling, Ralph; Egrie, Joan C.; Chen, Kenneth K.; Fox, Gary M.; Martin, Frank; Stabinsky, Zippora; Badrawi, Sayed M.; Lai, Por–Hsiung; Goldwasser, Eugene. Cloning and expression of the human erythropoietin gene. Proc. Natl. Acad. Sci. USA, vol. 82, pp. 7580–7584, Nov. 1985.

Markham, Anthony; Bryson, Harriet M. Epoetin Alfa, A Review of its Pharmacodynamic and Pharmacokinetic Properties and Therapeutic Use in Nonrenal Applications. Drugs 49 (2): 232–254, 1995.

McMahon, Gilbert F.; Vargas, Ramon; Michael; Jain, Adesh K.; Abels, Robert I.; Perry, Barbara; Smith, Ian L. Pharmacokinetics and Effects of Recombinant Human Erythropoietin After Intravenous Subcutaneous Injections in Heathy Volunteers. Blood, vol 76, No. 9 (Nov. 1): pp 1718–1722, 1990.

Salmonson, T.; Danielson, B.G,; Wikstrom, B. The pharmacokinetics of recombinant human erythropoeitin after intravenous and subcutaneous administration to healthy subjects. Br. J. clin. Pharmac., 29, 709–713, (1990).

* cited by examiner

PHARMACEUTICAL COMPOSITIONS OF ERYTHROPOIETIN

CROSS-REFERENCE TO RELATED APPLICATION

This application claims priority from United States provisional application Serial No. 60/128,596, filed Apr. 9, 1999, the contents of which are hereby incorporated by reference.

FIELD OF THE INVENTION

The present invention provides aqueous pharmaceutical formulations of erythropoietin that are free of human serum blood products, stabilized with a quantity of an amino acid and a sorbitan mono-9-octadecenoate poly(oxy-1,2-ethanediyl) derivative. The present invention also provides aqueous stable, preserved pharmaceutical formulations of erythropoietin that contain an antimicrobial quantity of cresol and a quantity of an amino acid.

BACKGROUND OF THE INVENTION

Erythropoietin (EPO) is a glycoprotein hormone secreted by the kidneys in response to tissue hypoxia, which stimulates red blood cell production in the bone marrow (1). The gene for EPO has been cloned and expressed in Chinese hamster ovary cells (2,3). This recombinant human erythropoietin (epoetin alfa, rhEPO) has an amino acid sequence identical to that of human urinary erythropoietin, and the two are indistinguishable on the basis of functional and immunological assays, although differences exist regarding protein glycosylation, affecting in vivo efficacy (4,5).

In clinical trials to date, rhEPO has been evaluated in normal subjects as well as in patients with various anemic conditions (6,7). EPO induces a brisk hematologic response in normal human volunteers, provided that adequate supplies of iron are available to support increased hemoglobin synthesis (8). The majority of trials have investigated the safety and effectiveness of rhEPO in the treatment of chronic renal failure maintained on dialysis and in those not yet on maintenance dialysis. Other indications approved in the US include anemia secondary to chemotherapy treatment in cancer and anemia associated with zidovudine treatment of human immunodeficiency virus infection. Worldwide, EPO has been used to treat anemia associated with rheumatoid arthritis, prematurity, myelofibrosis, sickle cell anemia, bone marrow transplantation, thermal injury, β-thalassemia, as a facilitator of presurgical autologous blood donation, and use as a presurgical adjuvant (6,7).

Although rhEPO is generally well tolerated, occasional skin rashes and urticaria have been observed suggesting allergic hypersensitivity to some components of the Epoetin alfa formulation, likely human serum albumin. Further, despite blood screening, there exists a risk of infection with a transmissible agent when a pharmaceutical agent is formulated using human blood products. Therefore pharmaceutical formulations of rhEPO that are stable and are free of human blood products, such as albumin are needed.

U.S. Pat. No. 4,992,419 describes lyophilized formulations of erythropoietin containing 5 to 50 g/L urea, 1 to 50 g/L amino acids, 0.05 to 5 g/L surfactants, and without human serum albumin. Aqueous formulations are described, but show a limited stability compared to formulations containing human serum albumin, and thus are not practical commercially. Hence the end user, either a physician or patient, must reconstitute the formulation immediately prior to administration. Lyophilized formulations are not preferred in a clinical formulation of erythropoietin because the reconstitution process is time consuming, poses risks of improper handling of the protein formulation, or may be reconstituted improperly and certain additives such as stabilizers are usually required to retain sufficient activity of the drug. Hence aqueous formulations of erythropoietin are generally preferred.

U.S. Pat. No. 5,376,632 describes aqueous, lyophilized, or spray-dried formulations or erythropoietin containing β or γ cyclodextrins and not containing other additional stabilizers such as human serum albumin, bovine serum albumin, lecithin, methyl cellulose, polyethylene glycol, sulfur containing reducing agents, urea, amino acids, and surfactants (col 4 lines 51–54).

U.S. Pat. No. 5,661,125 describes aqueous formulations of erythropoietin containing antimicrobial preservatives such as benzyl alcohol, parabens, phenols, and mixtures thereof. Formulations free of human serum albumin were prepared and examined for stability relative to corresponding human serum albumin containing formulations. The results indicated significant precipitation of erythropoietin in HSA-free cresol (0.5%) and chlorocresol (0.3%) formulations, even at 0° C. (col 8. lines 1–29), thus rendering these formulations clinically impractical. Further, EPO formulations containing cresol used in the range of 0.2–0.5% are described as having poor accelerated stability and a more rapid decay of EPO (col 6, lines 21–25). Current commercially available preserved multidose formulations contain 1- % benzyl alcohol.

Commercially available rhEPO formulations are prepared in citrate buffer in strengths of 1000 IU/0.5 mL, 2000 IU/mL, 5000 IU/mL, and 10,000 IU/mL (10K) for both intravenous (iv) and subcutaneous (sc) injection. These formulations are clinically documented to commonly cause patient discomfort associated with s.c. administration of the citrate-buffered formulations (9,10). As the predominant clinical use of rhEPO was switched from i.v. to s.c., it soon became evident that the local tolerance of the present formulation was not optimal. Neither adapting the drug to room temperature before injection nor avoiding volumes in excess of 1 ml were sufficient to prevent pain at the injection site. As neither human albumin, which is used as a stabilizer of the formulation, nor low osmolality of the solution were found to be pain inducers, the citrate buffer of rhEPO was a suggested candidate. A 40,000 IU/ml, single dose, preservative free formulation is commercially available that contains sodium phosphate, rather than citrate buffer. There is a need for stable, smaller dose formulations that contain phosphate buffer instead of the less preferable citrate buffer.

SUMMARY OF THE INVENTION

The present invention provides pharmaceutical formulations of erythropoietin comprising: (a) a pH buffering agent; (b) a stabilizing amount of a sorbitan mono-9-octadecenoate poly(oxy-1,2-ethanediyl) derivative; (c) a stabilizing amount of an amino acid; and (d) a pharmaceutical quantity of erythropoietin; wherein the formulation does not contain urea or a human blood product. Preferred formulations comprise combinations of polysorbate 80 and glycine as stabilizing agents. Particularly preferred formulations comprise combinations of polysorbate 80 and glycine as stabilizing agents in a phosphate buffer system.

The present invention also provides pharmaceutical formulations of erythropoietin comprising: (a) a pH buffering agent; (b) a stabilizing amount of human serum albumin; (c)

a stabilizing amount of an amino acid; (d) a antimicrobial quantity of cresol; and (e) a pharmaceutical quantity of erythropoietin. Preferred formulations comprise combinations of human albumin and glycine as stabilizing agents. Particularly preferred formulations comprise combinations of human serum albumin and glycine as stabilizing agents in a phosphate buffer system with m-cresol used at a concentration of about 0.3%.

Formulations of the present invention display pharmacokinetic properties similar to the current pharmaceutical products, such as absorption, disposition and serum concentration levels similar to currently marketed pharmaceutical formulations of recombinant human erythropoietin. Further, formulations of the present invention present less intense discomfort to the patient upon administration and exhibit much shorter duration of discomfort at the injection site. Hence the present invention provides human serum albumin free or preserved pharmaceutical formulations of erythropoietin that can be used for erythropoietin and may be formulated to reduce patient discomfort.

DETAILED DESCRIPTION

Figure 1:
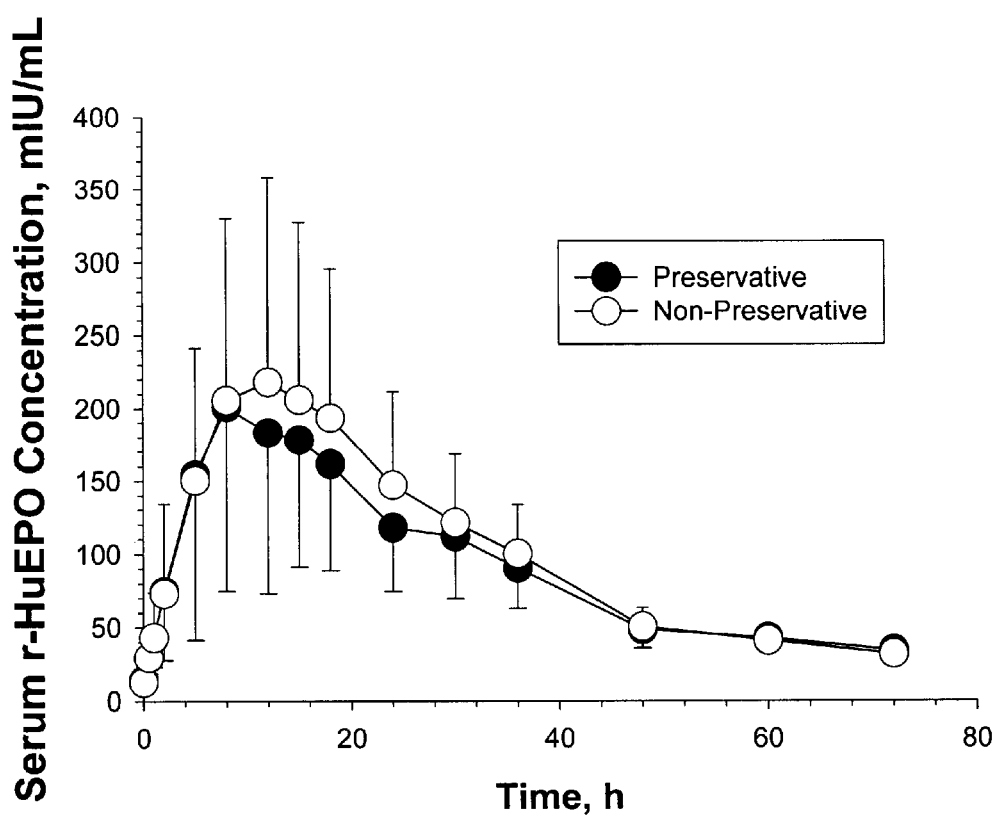
FIG. 1—Mean serum erythropoietin concentration-time profiles (uncorrected for baseline erythropoietin levels) for subjects receiving a single 150 IU/kg s.c. dose of rhEPO with and without 0.3% m-cresol preservative. Serum erythropoietin concentrations were determined by radioimmunoassay (RIA).

The present invention provides stable aqueous pharmaceutical formulations of erythropoietin that contain amino acids and sorbitan mono-9-octadecenoate poly(oxy-1,2-ethanediyl) derivatives stabilizing agents in a buffer free from human blood products or urea. Hence the present invention provides pharmaceutical formulations of erythropoietin comprising:

(a) a pH buffering agent;
(b) a stabilizing amount of sorbitan mono-9-octadecenoate poly(oxy-1,2-ethanediyl) derivative;
(c) a stabilizing amount of an amino acid;
(d) a pharmaceutical quantity of erythropoietin; and
wherein the formulation does not contain urea or a human blood product.

The present invention also contemplates cresol preserved aqueous formulations of erythropoietin stabilized with a combination of human serum albumin and an amino acid. Accordingly, the present invention provides pharmaceutical formulations of erythropoietin comprising:

(a) a pH buffering agent;
(b) a stabilizing amount of human serum albumin;
(c) a stabilizing amount of an amino acid;
(d) a antimicrobial quantity of cresol; and
(e) a pharmaceutical quantity of erythropoietin.

One goal for these formulations was to minimize the clinically documented patient discomfort associated with subcutaneous administration of the citrate-buffered formulations. Therefore phosphate buffer systems are particularly preferred in all formulations of the present invention.

The amount of buffering agent useful in the pharmaceutical compositions of the present invention depend largely on the particular buffer used and the desired pH of the formulation. The preferred pH range for the solutions is between about 5–8 with about 6–7.5 being more preferred, and a pH of about 6.9 being most preferred. Over these pH values, the amount of buffers will generally range from about 10 mM to about 30 mM. The use of a buffer system of sodium phosphate dibasic and sodium phosphate monobasic is preferred. Other suitable buffer systems to maintain the desired pH range of about 5 to about 8 include but are not limited to sodium citrate/citric acid, sodium acetate/acetic acid, and any other pharmaceutically acceptable pH buffering agent known in the art.

There may be added a pH-adjusting agent such as, but not limited to hydrochloric acid, citric acid, sodium hydroxide, or a salt of any of these, in particular sodium citrate may be used for this purpose.

The tonicity agent useful in the formulations of the present invention is any agent capable of rendering the formulations of the present invention isoosmotic with human blood. Typical suitable tonicity agents are well known in the art, and include but are not limited to sodium chloride, mannitol, glycine, glucose and sorbitol. Use of sodium chloride as a tonicity agent is preferred in the formulations of the present invention.

The sorbitan mono-9-octadecenoate poly(oxy-1,2-ethanediyl) derivatives, including but not limited to, polysorbate 80 or polysorbate 20 are examples of derivatives useful as stabilizing agents to prevent adsorption of the erythropoietin onto the surfaces of containers holding formulations containing erythropoietin. A wide variety of sorbitan mono-9-octadecenoate poly(oxy-1,2-ethanediyl) derivatives are known in the art and are useful in the formulations of the present invention. The amount of polysorbate 20 or 80 useful in the formulations of the present invention is in the range of about 0.01 to about 1.0 mg per mL for a formulation containing 1000–100,000 IU per vial of erythropoietin. The use of polysorbate 80 is preferred with the use of 0.3 mg/mL of polysorbate 80 being more preferred in the formulations of the present invention.

Amino acids, including but not limited to glycine, L-isoleucine, L-leucine, L-2-phenylalanine, L-glutamic acid, and L-threonine, are used in the amounts from 0.1 g/L to 50 g/L, and preferably in the amounts from 0.25 g/L to 20 g/L. L-alanine and L-arginine are not preferred in the formulations of the present invention because their inclusion causes conformational changes to the structure of EPO. Glycine is the preferred amino acid, and is preferably used in the amount of 0.25 g/L to 20 g/L, and particularly 0.5 g/L in formulations containing polysorbate 80 and lacking human serum albumin. Glycine is the preferred amino acid, and is preferably used in the amount of 0.5 g/L to 50 g/L, and particularly 2.0 g/L in formulations containing human serum albumin and preserved with cresol. In the formulations of the present invention, any amino acid in either the L- or D-isomeric form is suitable for use, with the exception of L-arginine and L-alanine.

Particularly preferred compositions are selected from the group consisting of those

TABLE A

| Formula Description | Active ingredient | Inactive Ingredients |
|---|---|---|
| 2000 IU/ml HSAfree | 2000 IU EPO | 4.38 mg Sodium Chloride<br>1.16 mg Sodium phosphate monobasic dihydrate<br>2.23 mg Sodium phosphate dibasic dihydrate<br>5.00 mg Glycine<br>0.30 mg Polysorbate 80<br>adjust to 1.0 mL with Water for injection |
| 4000 IU/ml HSAfree | 4000 IU EPO | 4.38 mg Sodium Chloride<br>1.16 mg Sodium phosphate monobasic dihydrate<br>2.23 mg Sodium phosphate dibasic dihydrate<br>5.00 mg Glycine<br>0.30 mg Polysorbate 80<br>adjust to 1.0 mL with Water for injection |
| 10,000 IU/ml HSAfree | 10000 IU EPO | 4.38 mg Sodium Chloride<br>1.16 mg Sodium phosphate monobasic dihydrate<br>2.23 mg Sodium phosphate dibasic dihydrate<br>5.00 mg Glycine<br>0.30 mg Polysorbate 80<br>adjust to 1.0 mL with Water for injection |
| 40,000 IU/ml HSAfree | 40000 IU EPO | 4.38 mg Sodium Chloride<br>1.16 mg Sodium phosphate monobasic dihydrate<br>2.23 mg Sodium phosphate dibasic dihydrate<br>5.00 mg Glycine<br>0.30 mg Polysorbate 80<br>adjust to 1.0 mL with Water for injection |

TABLE B

| Formula Description | Active ingredient | Inactive Ingredients |
|---|---|---|
| 10,000 multidose preserved w/ cresol | 10000 IU EPO | 6.25 mg Human serum albumin<br>2.91 mg Sodium phosphate monobasic dihydrate<br>11.19 mg Sodium phosphate dibasic dodecahydrate<br>50.00 mg Glycine<br>7.50 mg m-Cresol<br>ad to 2.5 ml with Water for injection |
| 25,000 multidose preserved w/ cresol | 25000 IU EPO | 6.25 mg Human serum albumin<br>2.91 mg Sodium phosphate monobasic dihydrate<br>11.19 mg Sodium phosphate dibasic dodecahydrate<br>50.00 mg Glycine<br>7.50 mg m-Cresol<br>ad to 2.5 ml with Water for injection |
| 40,000 multidose preserved w/ cresol | 40000 IU EPO | 5.00 mg Human serum albumin<br>2.33 mg Sodium phosphate monobasic dihydrate<br>8.95 mg Sodium phosphate dibasic dodecahydrate<br>40.00 mg Glycine<br>6.00 mg m-Cresol<br>ad to 2.0 ml with Water for injection |

Surprisingly it was found that aqueous formulations of erythropoietin using a phosphate buffer system containing an amino acid and sorbitan mono-9-octadecenoate poly (oxy-1,2-ethanediyl) derivative and not containing urea or a human blood product provided stable formulations. In particular, formulations containing glycine and polysorbate 80 provide excellent and unexpected stability compared to previous formulations described in the art.

The erythropoietin is present in the compositions in therapeutically effective amounts. "Erythropoietin" shall include those proteins that have the biological activity of human erythropoietin, as well as erythropoietin analogs, erythropoietin isoforms, erythropoietin mimetics, erythropoietin fragments, hybrid erythropoietin proteins, fusion proteins oligomers and multimers of the above, homologues of the above, glycosylation pattern variants of the above, and muteins of the above, regardless of the biological activity of same, and further regardless of the method of synthesis or manufacture thereof including but not limited to, recombinant whether produced from cDNA or genomic DNA, synthetic, transgenic, and gene activated methods. Specific examples of erythropoietin include, Epoetin alfa (EPREX®, ERYPO®), Novel erythropoiesis stimulating protein (NESP) (a hyperglycosylated analog of recombinant human erythropoietin (Epoetin) described in European patent application EP640619), human erythropoietin analog—human serum albumin fusion proteins described in the international patent application WO9966054, erythropoietin mutants described in the international patent application WO9938890, erythropoietin omega, which may be produced from an Apa I restriction fragment of the human erythropoietin gene described in U.S. Pat. No. 5,688,679, altered glycosylated human erythropoietin described in the international patent application WO9911781, PEG conjugated erythropoietin analogs described in WO9805363 or U.S. Pat. No. 5,643,575. Specific examples of cell lines modified for expression of endogenous human erythropoietin are described in international patent applications WO9905268 and WO9412650.

The effect of erythropoietin maybe monitored by measuring the hematocrit with the target hematocrit range being 30–33%. Dose adjustment may be made by monitoring the hematocrit. The single use vials of erythropoietin contain 2,000, 3,000 4,000 10,000, or 40,000 units of erythropoietin (1 IU corresponds to about 8.4 nanograms recombinant erythropoietin). As the formulations in one embodiment of the present invention are preserved and provide the benefit of being multi-dose, the formulations preferably will contain a multiple many times the number of units of erythropoietin present in a single use vial. Compositions containing 1,000–100,000 units or more of erythropoietin per vial are included within the present invention. In general it is contemplated that an effective amount will be from about 1 to 500 I.U./kg body weight and more preferably from 50 to 300 I.U./kg body weight especially erythropoietin given sc. The effective amount will further depend on the species and size of the subject being treated, the particular condition or disease being treated and its severity and the route of administration. In any case the dose to be used should be non-toxic to the host.

Surprisingly it was discovered that erythropoietin could be formulated as a preserved stable aqueous formulation containing <0.5% cresol and containing human serum albumin and an amino acid as stabilizing agents. The preferred range of cresol is 0.2%–0.5%, with 0.3% being most preferred. Glycine is the preferred amino acid stabilizer. The present invention provides a cresol preserved, phosphate-buffered formulations, developed in 10,000 IU/2.5 mL, 25,000 IU/2.5 mL, and 40,000 IU/2.0 mL (40K) strengths. The higher unit dose formulation reduces the number of subcutaneous injections and improve patient compliance.

Data from example 1 of the present invention indicates that the use of citrate or phosphate as the buffer and the inclusion of m-cresol in the formulation had not caused a decrease in the absorption and disposition characteristics as well as the safety profiles of erythropoietin. Therefore, it can be concluded that the new preserved multidose erythropoietin phosphate-buffered formulation is comparable to the currently marketed single-use formulations, and the multidose erythropoietin can be used in all indications currently approved for erythropoietin.

Being pharmacokinetically comparable to the single-use EPREX formulations, the new formulation is therefore expected to be clinically comparable also. Moreover, the phosphate-buffered multidose erythropoietin has a potential additional benefit over the single-use erythropoietin vials; one of economy. The use of erythropoietin for treatment of anemia or autologous blood predeposit requires repeated administrations of the hormone once every 4 weeks, one every 2 weeks, one-a-week, twice-a-week, or three-times-a-week. Being designed for single usage, any unused portion of the single-use erythropoietin must be discarded; whereas, by using the proper size of the preserved multidose erythropoietin, the amount of erythropoietin that will be discarded will be minimized. In addition, the bacteriocidal property of the preserved formulations of the present invention make it more suitable for potential self-administration and for treating multiple patients in institutional settings, translating into significant savings in health care costs. The multidose erythropoietin vials will also provide additional convenience in drug administration by minimizing the number of single-use vials and ampoules that the patient/health care providers have to utilize at high dosage volumes. The higher strengths (25,000 IU/2.5 mL and 40,000 IU/2.0 mL) of the multidose erythropoietin may also minimize injection volumes, especially for those indications that require higher doses. The multidose erythropoietin may also enable a single vial to be used for a dose administration. For example, the recommended dosage for autologous blood donation program is 600 IU/kg twice weekly (7). For a 70 kg patient, the recommended dosage regimen will be about 40K twice weekly. In such a case, a single 40K vial can be used for a single drug administration.

The following examples illustrate the present invention without, however, limiting the same thereto.

EXAMPLE 1

The 10,000 IU strength of the formulation was chosen in the study illustrated in Example 1 because this strength provided a reasonable, as well as the maximally recommended, sc injection volume of about 1 mL. By minimizing the injection volume, the higher strengths of the multidose erythropoietin potentially enable the reduction of the number of sc injection sites, which is a clear advantage in improving patient compliance.

Objective

To compare the safety and pharmacokinetics of subcutaneously administered recombinant human erythropoietin (epoetin alfa, rhEPO) formulated in a phosphate buffer and containing 0.3% m-cresol preservative (10,000 IU/mL) with the commercially available citrate-buffered rhEPO formulation (without preservative).

Patients and Methods

Patients

Eighteen healthy volunteers ranged in age between 20–38 years of age (mean age 26.9 years) and weighed between 60.8–87.4 kg (mean weight 72.3 kg) were enrolled and completed this study. The mean age of Group I subjects (28.1 years) was slightly older than that of Group II subjects (25.8 years), although this difference was not expected to affect the study results. The subjects enrolled in this study had no clinically significant abnormal laboratory values for hematology or serum chemistry. They had negative urine toxicology screen, HIV screen, and hepatitis B surface antigen. They did not have any evidence of the following: hypertension (e.g., diastolic blood pressure $\geq$ 95 mm Hg); a history of any primary hematologic disease; history of significant hepatic, renal, cardiovascular, gastrointestinal, genitourinary, metabolic, neurologic disease; a history of anemia or seizure disorder; a known sensitivity to mammalian-derived products or human serum albumin; habitual and heavy consumer to beverages containing caffeine; participation in any other clinical trial or had blood transfused or donated within 30 days of study entry; had exposure to rhEPO within three months of study entry; had an illness within seven days of study entry; and have significant abnormalities on the pre-study physical examination or the clinical laboratory evaluations within 14 days of study entry. All subjects were evaluable for safety and all blood collections for pharmacokinetic analysis were collected as scheduled. All studies were performed with institutional ethics committee approval and patient consent.

Study Design

This was a Phase I, single-center, open-label, randomized, two-period crossover study in healthy male volunteers. Eighteen subjects were randomly assigned to one of two treatment sequence groups (nine subjects/group). RhEPO was administered over two separate dosing periods as a bolus s.c. injection in the upper thigh. Each dosing period was separated by a 14-day washout period. Subjects were confined to the study center at least 12 hours prior to and 72 hours following dosing for each of the two dosing periods, but not between dosing periods. The dosing regimen is summarized in Table 1.

TABLE 1

Dosage regimen and study design

| Group | N | Period 1 | Washout Period | Period 2 |
|---|---|---|---|---|
| I | 9 | Single dose of 150 IU/kg rhEPO s.c. with m-cresol preservative | 14 days | Single dose of 150 IU/kg rhEPO s.c. without m-cresol preservative |
| II | 9 | Single dose of 150 IU/kg rhEPO s.c. without m-cresol preservative | 14 days | Single dose of 150 IU/kg rhEPO s.c. with m-cresol preservative |

Two formulations of EPO were used in this study. Epoetin alfa (marketed as EPREX®) contains rhEPO 10,000 IU/mL in citrate buffer. The rhEPO formulation with preservative contains rhEPO 25,000 IU/2.5 mL in phosphate buffer with m-cresol preservative.

Blood Sampling

Serial blood was drawn by direct venipuncture before and after administration of EPO. Venous blood samples (5 mL) for determination of serum erythropoietin concentrations were obtained at ~30, 20, and 10 minutes prior to dosing (3 baseline samples) and at approximately the following times after dosing: 30 minutes and at 1, 2, 5, 8, 12, 15, 18, 24, 30, 36, 48, 60 and 72 hours. Each serum sample was divided into two aliquots. All serum samples were stored at −20° C. Serum samples were shipped on dry ice. Fasting clinical laboratory tests (hematology, serum chemistry, and urinalysis) were performed immediately prior to the initial dose on day 1, the morning of day 4, immediately prior to dosing on day 16, and the morning of day 19.

Bioanalytical Methods

A radioimmunoassay (RIA) kit procedure (Diagnostic Systems Laboratory [DSL], Webster TX), was used for the determination of serum erythropoietin concentrations. The commercially available RIA is a double-antibody, competitive method that uses a rabbit polyclonal antiserum to human urinary erythropoietin as the primary antibody and an $^{125}$I-labeled human urinary erythropoietin as the tracer. Epoetin alfa was substituted for urinary erythropoietin provided in the DSL kit, in standards and quality control samples. Standard concentrations used in the assay were 7.8, 15.6, 31.3, 50, 62.5,1 00, and 125 mIU/mL. Sensitivity, defined as the mean back-fit value for the lowest standard giving acceptable precision, was 8.6 mIU/mL, and the assay range was extended to 2,000 mIU/mL through quality control dilutions.

Safety Determinations

Vital signs were recorded immediately prior to each dosing (Days 1 and 16), and at 6, 24, 48, and 72 hours after each dosing. Safety determinations were based on the incidence and type of adverse events and the changes in clinical laboratory tests from baseline. In addition, changes from pre-study in vital sign measurements, including blood pressure, and physical examination results were evaluated.

Data Analysis

Post-dose serum concentration values were corrected for pre-dose baseline erythropoietin concentrations by subtracting from each of the post-dose values the mean baseline erythropoietin concentration determined from averaging the erythropoietin levels from the three samples collected at 30, 20, and 10 minutes before dosing. Pre-dose serum erythropoietin concentrations were not included in the calculation of the mean value if they were below the quantification level of the assay. Pharmacokinetic parameters were determined from serum concentration data corrected for baseline erythropoletin concentrations.

Pharmacokinetic parameters were calculated by model independent methods on a Digital Equipment Corporation VAX 8600 computer system using the BIOAVL software Version 8.0 (Scientific Computer Systems, RWJPRI). The following pharmacokinetics parameters were determined: peak serum concentration ($C_{max}$); time to peak serum concentration ($t_{max}$); area under the concentration-time curve (AUC) from time zero to the last blood sampling time ($AUC_{0-72}$) calculated with the use of the linear trapezoidal rule; and terminal elimination half-life ($t_{1/2}$), computed from 0.693/elimination rate constant. The elimination rate constant was estimated by linear regression of consecutive data points in the terminal linear region of the log-linear concentration-time plot. The mean, standard deviation (SD), and coefficient of variation (CV) of the pharmacokinetic parameters were calculated for each treatment. The ratio of the parameter means (preserved formulation/non-preserved formulation) was calculated.

Results

Safety Results

The incidence of adverse events was equally distributed across the treatment groups (39%, rhEPO without preservative; 33%, rhEPO with preservative). There were no clinically significant changes from baseline or pre-study clinical laboratory tests or blood pressures, and no notable changes from pre-study in physical examination results and vital sign measurements. It is of interest that mean total bilirubin decreased to almost half the baseline value by Day 4 following therapy. However, the magnitude of this decrease was similar in both treatment groups, and mean total bilirubin levels remained within the normal range. Similar changes in other liver function tests (alkaline phosphatase, SGOT, SGPT, LDH) were not noted. Thus, the safety profiles for the two treatment groups appeared similar.

Pharmacokinetic Results

Mean serum erythropoietin concentration-time profiles (uncorrected for baseline erythropoietin levels) in all 18 subjects after receiving a single 150 IU/kg s.c. dose of rhEPO with and without m-cresol preservative were comparable at each time point measured (FIG. 1). All subjects had pre-dose baseline erythropoietin concentrations within the normal physiologic range (<8.6 to 22 mIU/mL).

Pharmacokinetic parameters were determined from serum data corrected for pre-dose mean baseline erythropoietin concentrations (Table 2). $C_{max}$ ranged from a low of 85 mIU/mL to a high of 558 mIU/mL (mean 198±123 mIU/mL) for rhEPO with preservative and from 61 mIU/mL to a high of 601 mIU/mL (mean 226±138 mIU/mL) for rhEPO without preservative. Of note, two subjects had unusually high $C_{max}$ values (i.e., Subject 111 for rhEPO with preservative [558 mIU/mL] and Subject 118 for rhEPO without preservative [601 mIU/mL]) compared with the other 16 subjects (i.e., <400 mIU/mL). When $C_{max}$ was calculated without these two values, the mean $C_{max}$ values for the rhEPO formulations with and without preservative were more comparable (177±89 and 196±102 mIU/mL, respectively).

For the rhEPO formulation with preservative, the mean erythropoietin $AUC_{(0-72\ hr)}$ was 5,754±2,284 mIU·h/mL, ranging from 2,973 to 11,185 mIU·h/mL. Similarly, the rhEPO formulation without preservative had a mean erythropoietin of $AUC_{(0-72\ hr)}$ of 6,521±2,769 mIU·h/mL, ranging from 3,096 to 14,235 mIU·h/mL.(Table 2). Of note, two subjects had unusually high $AUC_{(0-72\ hr)}$ values (i.e., Subject 111 for rhEPO with preservative [11,185 mIU·h/mL] and Subject 118 for rhEPO without preservative [14,235 mIU·h/mL]) compared with the other 16 subjects (i.e., <10,000 mIU/mL). When $AUC_{(0-72\ hr)}$ was calculated without these two values, the mean $AUC_{(0-72\ hr)}$ values for rhEPO formulations with and without preservative were more comparable (5,460±1960 and 6,000±2,100 mIU/mL, respectively).

The mean $t_{max}$ was similar for rhEPO with and without preservative (12±5 and 13±5 h, respectively). The range for the $t_{max}$ was similar for both rhEPO formulations (8–24 h). Terminal half-life values were similar for rhEPO with and without preservative (20.2±8.1 and 19.8±6.6 h, respectively).

Terminal half-life values observed in both parts of this study (~20 h) were similar to those after sc injection reported in the literature (11,12). These half-life values, however, were longer than those observed previously after iv administration (~5 h) (11–14). These longer half-life values were not unexpected if the rate of absorption from the injection site, rather than the rate of elimination, is the rate-limiting step.

TABLE 2

Mean ± SD (% CV) pharmacokinetic parameters following a single 150 IU/kg s.c. dose of rhEPO with and without 0.3% m-cresol preservative

| Parameter | rhEPO with 0.3% m-cresol | rhEPO without 0.3% m-cresol | Ratio[a] |
|---|---|---|---|
| $C_{max}$ (MiU/mL) | 198 ± 123 (62.1%) | 226 ± 138 (61.1%) | 0.88 |
| $t_{max}$ (hr) | 12 ± 5 (41.1%) | 13 ± 5 (35.7%) | 0.92 |
| $AUC_{(0-72)}$ (IU · h/mL) | 5.75 ± 2.28 (39.7%) | 6.52 ± 2.77 (42.5%) | 0.88 |
| $t_{1/2}$ (h) | 20.2 ± 8.1 (40.2%) | 19.8 ± 6.6 (33.2%) | 1.02 |

[a]Parameter ratio, rhEPO with m-cresol/rhEPO without m-cresol

Although the present study was conducted in healthy male subjects, similar absorption characteristics and safety profiles would be anticipated in other patient populations; such as male or female patients with cancer or chronic renal failure, pediatric renal failure patients, patients in autologous predeposit programs, or patients scheduled for elective surgery.

In conclusion, subcutaneously administered single doses of rhEPO (150 IU/kg) with or without 0.3% m-cresol preservative were safe and well tolerated by healthy male subjects. Based on a comparative incidence of adverse events, clinical laboratory values, vital signs, and physical examination results, the safety profiles of rhEPO formulated with and without preservative were equivalent. The proposed multiple strengths of the new multidose EPREX potentially provides large clinical utility to patients and health care providers.

EXAMPLE 2

Comparative Safety, Tolerance and Pharmacokinetics of Two Formulations of Reconbinant Human Erythropoietin Formulated With or Without a New Stabilizer After Single Subcutaneous Administration in Healthy Subjects Objective To compare the safety, tolerance, and pharmacokinetics of two concentrations (2,000 [lowest currently made] and 40,000 IU/mL [highest currently made]) of phosphate-buffered recombinant human erythropoietin (EPREX®, epoetin alfa, rhEPO) formulated with a new stabilizer (glycine and Polysorbate 80) with the commercially available EPREX® formulations, which uses human serum albumin (HSA) as the stabilizer.

Patients and Methods

Patients

Twenty-four volunteers ranged in age between 18–35 years of age (mean age 21.9 years), weighed between 57.2–92.3 kg (mean weight 74.3 kg) were enrolled in the first study. The mean ages of the two treatment sequence groups in the first study were very similar (21.8 and 22.0 years). Twenty-three of these 24 subjects completed the study. One subject completed all assessments for the first dosing period but decided not to return for the second dosing period. The safety and tolerance data from this subject, who received only the rhEPO without the new stabilizer, were included in the safety data. The serum EPO concentration data from this subject, however, were not included in the pharmacokinetic analysis.

Another twenty-four male volunteers ranged in age between 18–40 years of age (mean age 23.8 years) and weighed between 62.2–93.4 kg (mean weight 73.1 kg) were enrolled and completed the second study. The mean ages of the two treatment sequence groups were very similar (24.5 and 23.1 years).

All subjects enrolled in these two studies had a pre-study hemoglobin not exceeding 16.0 g/dL; had no clinically significant abnormal laboratory values for hematology or serum chemistry; had negative urine toxicology screen, HIV screen, hepatitis B surface antigen, and hepatitis C antibodies. Subjects had no evidence of hypertension (e.g., sitting diastolic blood pressure >95 mm Hg); had no history of any primary hematologic disease; had no history of significant hepatic, renal, cardiovascular, gastrointestinal, genitourinary, metabolic, or neurologic disease; had no history of anemia or seizure disorder. Subjects were not sensitive to mammalian-derived products or HSA; were not habitual and heavy consumers of beverages containing caffeine; were not heavy smokers (>10 cigarettes/day); had not participated in any other clinical trial or had blood transfused or donated within 90 days of study entry; and had not been exposed to rhEPO within three months of study entry. All subjects were evaluable for safety and all blood collections for pharmacokinetic analysis were collected as scheduled. All studies were performed with institutional ethics committee approval and patient consent.

Study Design Both studies were Phase I, single-center, double-blind, randomized, two-period crossover studies in healthy male volunteers. In each study, 24 subjects were randomly assigned to one of two treatment sequence groups (12 subjects/group). EPO was administered over two separate dosing periods as a bolus s.c. injection in the upper thigh. Subjects were confined in the study center from 12 hours prior to dosing through at least 36 hours following dosing for each of the two dosing periods. Subjects returned to the study center for required assessments and blood sampling outside the confinement period. Each dosing period was separated by a 28-day washout period. Subjects were not confined between dosing periods (Days 3–29). Dosing regimens are summarized in Table 3.

TABLE 3

Dosage regimens and study designs

| Group | N | Period 1 (Day 1) | Washout Period | Period 2 (Day 30) |
|---|---|---|---|---|
| I | 12 | Single dose of 150 IU/kg rhEPO (2,000 IU/mL) s.c. without new stabilizer | 28 days | Single dose of 150 IU/kg rhEPO (2,000 IU/mL) s.c. with new stabilizer |
| II | 12 | Single dose of 150 IU/kg rhEPO (2,000 IU/mL) s.c. with new stabilizer | 28 days | Single dose of 150 IU/kg rhEPO (2,000 IU/mL) s.c. without new stabilizer |
| III | 12 | Single dose of 750 IU/kg rhEPO (40,000 IU/mL) s.c. without new stabilizer | 28 days | Single dose of 750 IU/kg rhEPO (40,000 IU/mL) s.c. with new stabilizer |
| IV | 12 | Single dose of 750 IU/kg rhEPO (40,000 IU/mL) s.c. with new stabilizer | 28 days | Single dose of 750 IU/kg rhEPO (40,000 IU/mL) s.c. without new stabilizer |

Two formulations of EPO were used in each study. The 2,000 IU/mL (2K) strength of the EPO with HSA as the stabilizer and the 2K strength of the new phosphate-buffered formulation of rhEPO contained glycine and Polysorbate 80 as the new stabilizer were used in the first study. In the second study, the 40,000 IU/mL (40K) strength of EPO with HSA as the stabilizer and the 40K strength of the new phosphate-buffered formulation of rhEPO contained the new stabilizer were used.

Blood Sampling

Serial blood was drawn by direct venipuncture before and after administration of EPO; a heparin lock was not employed. Venous blood samples (5 mL) for determination of serum erythropoietin concentrations were obtained at ~30, 20, and 10 minutes prior to dosing (3 baseline samples) and at approximately the following times after dosing: 0.5, 1, 2, 5, 8, 12, 15, 18, 24, 30, 36, 48, 60 and 72 hours (all groups). Subjects in the second study had additional blood samples drawn at 96, 120, 144, and 168 hours. Each serum sample was divided into two aliquots. All serum samples were stored at −20° C. Serum samples were shipped on dry ice. Fasting clinical laboratory tests (hematology, serum chemistry, and urinalysis) were performed immediately prior to the initial dose on Day 1, the morning of Day 4, immediately prior to dosing on Day 30, and the morning of Day 33.

Bioanalytical Methods

Sample analyses for serum erythropoietin levels were performed at LabCorp. A radioimmunoassay (RIA) kit procedure manufactured by Diagnostic Systems Laboratory (DSL), Webster, TX was used for the determination of serum erythropoietin concentrations. The commercially available RIA is a double-antibody, competitive method that uses a rabbit polyclonal antiserum to human urinary erythropoietin as the primary antibody and $^{125}$I-labeled human urinary erythropoietin as the tracer. The DSL kit was modified by substitution of epoetin alfa for urinary erythropoietin in standards and quality control samples. Standard concentrations used in the assay were 7.8, 15.6, 31.3, 50, 62.5, 100, and 125 mIU/mL. Sensitivity, defined as the mean back-fit value for the lowest standard giving acceptable precision, was 7.8 mIU/mL, and the assay range was extended to 5,000 mIU/mL through quality control dilutions.

Safety Determinations

Vital signs were recorded immediately prior to each dosing (Days 1 and 30), and at 6, 24, 30, 36, 48, 60, and 72 hours after each dosing. Safety determinations were based on the incidence and type of adverse events and the changes in clinical laboratory tests from baseline (up to 72 hours post-dosing). In addition, changes from pre-study in vital sign measurements, including blood pressure, and physical examination results were evaluated.

Tolerance Determinations

Tests to assess the tolerance at the site of injection were administered 45 minutes after each injection (Days 1 and 30). As each dose was divided into 3, 4 or 5 injections, the most painful injection site was assessed. There were two pain scales: a visual analog scale (VAS), consisting of a 10 cm horizontal line without gradations, and a verbal descriptive scale (VDS); consisting of five vertically placed boxes with adjacent descriptions. The end points of the VAS scale ranged from "no pain" to "the worst I can imagine", and those of the VDS scale ranged from "no pain" to "very severe pain". Subjects were then asked about pain duration. If the pain lasted longer than 45 minutes, the tolerance tests were to be administered at hourly intervals until return to normal.

Data Analysis

Post-dose serum concentration values were corrected for pre-dose baseline erythropoietin concentrations by subtracting from each of the post-dose values the mean baseline erythropoietin concentration determined from averaging the erythropoietin levels from the three samples collected at approximately 30, 20, and 10 minutes before dosing. Pre-dose serum erythropoietin concentrations were not included in the calculation of the mean value if they were below the quantification level of the assay. Pharmacokinetic parameters were determined from serum concentration data corrected for baseline erythropoietin concentrations.

Pharmacokinetic parameters were calculated by model independent methods using the WinNonlin software, Version 1.1 (Scientific Consulting, Inc). The following pharmacokinetic parameters were determined: peak serum concentration ($C_{max}$); time to peak serum concentration ($t_{max}$); area under the concentration-time curve (AUC) from time zero to the last blood sampling time $AUC_{(0-72)}$ [Groups I and II] and $AUC_{(0-168)}$ [Groups III and IV] calculated with the use of the linear trapezoidal rule; and terminal elimination half-life ($t_{1/2}$), computed from 0.693/elimination rate constant. The elimination rate constant was estimated by linear regression of consecutive data points in the terminal linear region of the log-linear concentration-time plot. A minimum of three data points was used in the regression. For those with correlation coefficients less than 0.975, the corresponding $t_{1/2}$ values were not EPOrted. The mean, standard deviation (SD), and coefficient of variation (CV) of the pharmacokinetic parameters were calculated for each treatment. The ratios of the mean pharmacokinetic parameters (rhEPO with the new stabilizer/rhEPO without the new stabilizer) were calculated.

Statistical analysis was carried out on both the raw and log-transformed bioavailability parameter, AUC. Analysis of variance models were fit to the raw AUC data and the log-transformed AUC data as the dependent variable and the effects due to treatment sequence group, subjects nested within the sequence groups, treatment, and period as predictors. Test for the treatment sequence group effect was carried out at the 10% level by using the mean square due to the subjects nested within sequence groups as the error term. The period effect was tested at the 5% level using the residual error term. The error mean square from the above model was used to estimate the intra-subject variability. The estimated least squares and intra-subject variability from the above model were used to construct 90% confidence intervals for the ratio of mean EPREX® with new stabilizer/mean HSA-containing EPREX.® Based on a CV of 40% obtained in a previous study, a sample size of 24 subjects should be sufficient to estimate the ratio within ±20% of the true value with 90% confidence. $C_{max}$, $t_{max}$, and $t_{1/2}$, both raw and transformed, were reported descriptively.

As non-planned statistical analyses, the three local tolerance parameters were analyzed by means of cross-over test methods (11). Before statistical testing could be performed, VAS scores and duration of pain values were transformed for normalization. The cross-over analyses for the transformed VAS and duration of pain values were performed using Proc glm within SAS®. The study design was specified with a 28-day washout period to eliminate the possibility of carry-over between dosing periods. Thus, the calculations were based on the standard crossover model without carry-over effect. The results of pain assessed with the VDS were analyzed by means of the Wilcoxon-Mann-Whitney rank sum test, according to the methods on crossover trials described by Koch et al. (12). In brief, this procedure consists of ranking the period differences for all of the patients in the trial and then using the Wilcoxon-Mann-Whitney test for differences between the two sequence groups.

Results
Safety Results

The overall incidence of adverse events was evenly distributed across all treatment groups. The incidence rates were 63% (rhEPO without new stabilizer) and 61% (rhEPO with new stabilizer) for the 2K strength and 54% (rhEPO without new stabilizer) and 46% (rhEPO with new stabilizer) for the 40K strength. All adverse events were transient and resolved without intervention, with the exception of paracetamol, which was given to five subjects for a mild headache or mild influenza-like symptoms (three receiving 2K rhEPO and two receiving 40K rhEPO). The most frequently EPOrted adverse event in all groups was headache.

Adverse events that were classified as possibly related to study medication in subjects receiving 40K strength rhEPO included: scaly skin (n=4), headache (n=2), myalgia (n=1), and tiredness (n=1). In the subjects receiving 2K strength rhEPO, adverse events that were possibly related to study medication included headache (n=2) and tiredness (n=2).

The four EPOrts of skin eruptions all occurred between three and eight days after administration of rhEPO with the new stabilizer; all events were mild and resolved within two to three days. With the exception of the four reports of scaly skin, no clinically significant differences in the type and incidence of adverse events were noted with either formulation for both rhEPO concentrations. There were no clinically significant changes over the first four days following administration of the study drug in clinical laboratory tests, blood pressures, physical examination results, and vital sign measurements with either formulation for both rhEPO concentrations. In all treatment groups, slight increases in reticulocytes were observed at Day 4 compared to baseline. Concomitantly, there were slight decreases in lymphocytes at Day 4 compared to baseline in all groups. There was a significant decrease in mean total bilirubin from baseline to Day 4 in all treatment groups. Minor changes in serum chemistry parameters were observed over the four days of study; however, none was considered to be clinically significant. Thus, the safety profiles for all four treatment groups appeared similar.

Tolerance Results

The mean VAS scores following a single 150 IU/kg s.c. dose of rhEPO (2K) with and without the new stabilizer did not differ significantly (p=0.608). Likewise, the mean VAS scores following a single 750 IU/kg s.c. dose of rhEPO (40K) with and without the new stabilizer did not differ significantly (p=0.402). When evaluating the VDS severity of pain by means of the Wilcoxon's rank sum test, the difference between the two formulations did not differ significantly (p=0.610) for subjects in Groups I and II and for subjects in Groups III and IV (p=0.581).

The overall mean duration of pain for all administrations of study drug was 1.01 minutes for subjects in Groups I and II and 3.03 minutes for subjects in Groups III and IV. The duration of pain was generally reported to last for three minutes or less for subjects in Groups I and II and for two minutes or less for subjects in Groups III and IV. The results for pain duration agreed with those obtained for the other tolerance parameters. No statistically significant difference in persistence of pain after injection was observed between subjects receiving EPREX® with and without the new stabilizer in Groups I and II (p=0.159) and Groups III and IV (p=0.951).

Comparison of pain between the two different concentrations of epeotin alfa revealed that pain was reported following all administrations of study medication (2K rhEPO) in Groups I and II. In contrast, no pain at all was reported in 24 out of 48 s.c. administrations (50%) in Groups III and IV subjects (40K rhEPO). In addition, the average pain scores (VAS, VDS) were greater following a single 150 IU/kg dose of rhEPO (2K) than following a single 750 IU/kg dose of rhEPO (40K). However, there was a higher incidence of pain as well as higher average pain scores reported following a single 150 IU/kg dose of rhEPO (2K) than a single 750 IU/kg dose of rhEPO (40K). This may be because more injections per administration of study drug were necessary in Groups I and II in order to achieve the required dose, due to the weaker formulation (2K) compared to that used in Groups III and IV (40K). It should also be noted that the needle used for both administrations to subjects in Groups I and II was narrower and more flexible than that used in subjects in Groups III and IV, which made it more difficult to administer s.c. injections. Lastly, the mean duration of pain was longer in Groups III and IV (40K) than Group I and II (2K), but this was probably due to two individuals receiving the 40K strength rhEPO who had longer lasting pain following both treatments compared to all subjects in all treatment groups.

Pharmacokinetic Results

Figure 2:
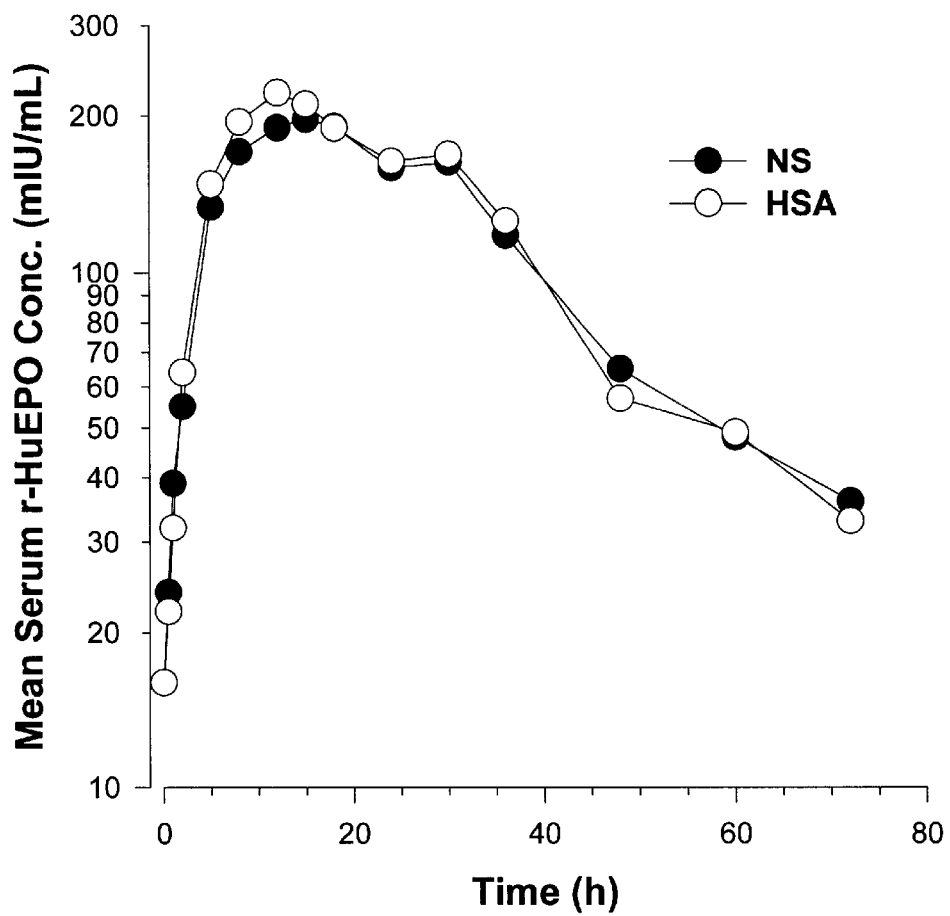
FIG. 2—Mean serum erythropoietin concentration-time profiles (uncorrected for baseline erythropoietin levels) for subjects receiving a single 150 IU/kg s.c. dose of rhEPO (2K) with and without new stabilizer. Serum erythropoietin concentrations were determined by radioimmunoassay (RIA).
Figure 3:
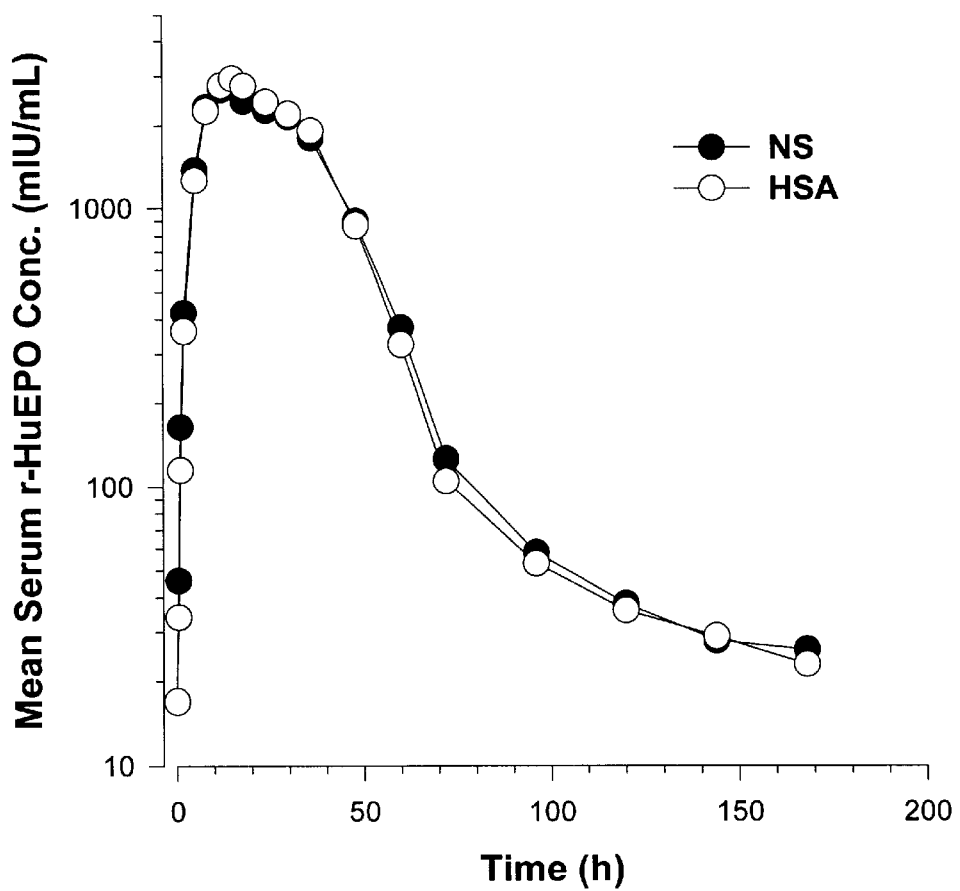
FIG. 3—Mean serum erythropoietin concentration-time profiles (uncorrected for baseline erythropoietin levels) for subjects receiving a single 750 IU/kg s.c. dose of rhEPO (40K) with and without new stabilizer. Serum erythropoietin concentrations were determined by RIA.

Mean serum erythropoietin concentration-time profiles in all subjects receiving either a single 150 IU/kg s.c. dose of rhEPO (Groups I and II) or a single 750 IU/kg s.c. dose of rhEPO (Groups III and IV) with and without the new stabilizer are shown in FIGS. 2 and 3, respectively (uncorrected for baseline erythropoietin concentrations). All subjects (n=48) had pre-dose baseline erythropoietin concentrations within the normal physiologic range (<7.8 to 32 mIU/mL). After a single 150 IU/kg s.c. dose of rhEPO (2K) with and without the new stabilizer, mean serum erythropoietin levels at Day 4 (36±11 and 33±11 mIU/mL, respectively) approached the mean pre-dose endogenous erythropoietin levels (16±6 and 16±7 mIU/mL, respectively). Similarly, after a single 750 IU/kg s.c. dose of rhEPO (40K) with and without the new stabilizer, mean serum erythropoietin levels at Day 7 (26±9 and 23±7, respectively) also approached mean pre-dose endogenous erythropoietin levels.

Pharmacokinetic parameters were determined from serum data corrected for pre-dose mean baseline erythropoietin concentrations. In Groups I and II, $C_{max}$ ranged from a low of 86.6 mIU/mL to a high of 681 mIU/mL (mean 222±128 mIU/mL) following a single 150 IU/kg s.c. dose of rhEPO (2K) with the new stabilizer and from 119 mIU/mL to a high of 377 mIU/mL (mean 226±79 mIU/mL) for rhEPO without the new stabilizer (Table 4). One subject who received a single dose of 150 IU/kg rhEPO (2K) with the new stabilizer had an unusually high $C_{max}$ value and one subject in the same group had an unusually low $C_{max}$ value. The reasons for these unusual $C_{max}$ values are not known. In Groups III and IV, $C_{max}$ ranged from a low of 1194 mIU/mL to a high of 4334 mIU/mL (mean 2978±808 mIU/mL) following a single 750 IU/kg s.c. dose of rhEPO (40K) with the new stabilizer and from 1892 mIU/mL to a high of 3997 mIU/mL (mean 3065±705 mIU/mL) for rhEPO without the new stabilizer (Table 5). There were no statistically significant differences (p<0.05) in $C_{max}$ between the rhEPO formulations with and without the new stabilizer for both the 2K and 40K strengths.

In Groups I and II, the $AUC_{(0-72)}$ ranged from a low of 3238 to a high of 11,318 (mean 6647±2488 mIU·h/mL) following a single 150 IU/kg s.c. dose of rhEPO (2K) with the new stabilizer. Similarly, the $AUC_{(0-72)}$ ranged from a low of 4234 to a high of 10,968 (mean 6983±1855 mIU·h/mL) following a single 150 IU/kg s.c. dose of rhEPO (2K) without the new stabilizer (Table 4). In Groups III and IV, the $AUC_{(0-168)}$ ranged from a low of 48,347 to a high of 136,290 (mean 102,768±21,500 mIU·h/mL) following a single 750 IU/kg s.c. dose of rhEPO (40K) with the new stabilizer. Similarly, the $AUC_{(0-168)}$ ranged from a low of 69,537 to a high of 136,689 (mean 104,897±15,781 mIU·h/mL) following a single 750 IU/kg s.c. dose of rhEPO (40K) without the new stabilizer (Table 5). There were no statistically significant differences (p <0.05) in $C_{max}$ between the rhEPO formulations with and without the new stabilizer for both the 2K and 40K strengths. Of note, the treatment sequence effect was statistically significant between rhEPO (40K) with the new stabilizer and rhEPO (40K) without the new stabilizer.

The mean $t_{max}$ was similar following a single 150 IU/kg s.c. dose of rhEPO (2K) with and without the new stabilizer (17.4±7.3 and 15.4±7.5 hr, respectively) (Table 4). Likewise, the mean $t_{max}$ following a single 750 IU/kg s.c. dose of rhEPO (40K) with and without the new stabilizer was 16.7±6.8 and 16.6±4.8 hr, respectively (Table 5). The $t_{max}$ ranged from 8–30 hours for both 2K rhEPO formulations. For the 40,000 IU/mL rhEPO concentration, the $t_{max}$ ranged from 8–36 hours for the formulation with the new stabilizer and 12–30 hours without the new stabilizer.

Although only a small percentage of subjects in Groups I and II had terminal half-life values reported, the values obtained were similar following a single 150 IU/kg s.c. dose of rhEPO (2K) with and without preservative (19.7±12.8 and 20.1±10.4 hr, respectively). Following a single 750 IU/kg s.c. dose of rhEPO (40K), terminal half-life values were similar with and without preservative (25.7±14.9 and 23.8±11.8 hr, respectively) in subjects in Groups III and IV.

TABLE 4

Mean ± SD (% CV) pharmacokinetic parameters following a single 150 IU/kg s.c. dose of rhEPO (2,000 IU/mL) with and without new stabilizer

| | Groups I and II | | | |
|---|---|---|---|---|
| Parameter | rhEPO without new stabilizer | rhEPO with new stabilizer | Ratio[a] | 90% Confidence Interval |
| $C_{max}$ (mIU/mL) | 226 ± 79 (34.5%) | 222 ± 128 (57.4%) | 0.98 | ND[b] |
| $t_{max}$ (hr) | 15.4 ± 7.5 (49.0%) | 17.4 ± 7.3 (41.8%) | 1.13 | ND |
| $AUC_{(0-72)}$ (mIU · h/mL) | 6983 ± 1859 (26.6%) | 6642 ± 2488 (37.4%) | 0.95 | 83.5–107[c] 81.1–105[d] |

[a]Parameter ratio, rhEPO with new stabilizer/rhEPO without new stabilizer
[b]Not Determined
[c]Raw data
[d]Log-transformed data

TABLE 5

Mean ± SD (% CV) pharmacokinetic parameters following a single 750 IU/kg s.c. dose of rhEPO (40,000 IU/mL) with and without new stabilizer

| | Groups III and IV | | | |
|---|---|---|---|---|
| Parameter | rhEPO without new stabilizer | rhEPO with new stabilizer | Ratio[a] | 90% Confidence Interval |
| $C_{max}$ (IU/mL) | 3065 ± 705 (23.0%) | 2978 ± 808 (27.1%) | 0.97 | ND[b] |
| $t_{max}$ (hr) | 16.6 ± 4.8 (29.1%) | 16.7 ± 6.8 (40.7%) | 1.00 | ND |

TABLE 5-continued

Mean ± SD (% CV) pharmacokinetic parameters following a
single 750 IU/kg s.c. dose of rhEPO (40,000 IU/mL) with and
without new stabilizer

| | Groups III and IV | | | |
|---|---|---|---|---|
| Parameter | rhEPO without new stabilizer | rhEPO with new stabilizer | Ratio[a] | 90% Confidence Interval |
| $AUC_{(0-168)}$ (mIU · h/mL) | 104,897 ± 15,781 (15.0%) | 102,768 ± 21,500 (20.8%) | 0.98 | 91.6–104[c] 89.8–104[d] |

[a]Parameter ratio, rhEPO with new stabilizer/rhEPO without new stabilizer
[b]Not Determined
[c]Raw data
[d]Log-transformed data EPREX® formulation with the glycine and Polysorbate 80 as the new protein stabilizer provides an alternative formulation for patients and health care providers for all the indications currently approved for EPREX.® The different strengths (i.e., 2K, 4K, 10K, and 40K) of EPO with the new stabilizer can be used interchangeably with all the different strengths.(i.e., 2K, 4K, 10K, and 40K) of the HSA-containing EPO.

EXAMPLE 3

Pharmacokinetics, Safety, and Tolerance Study of Two Formulations After Single subcutaneous Doses of Recombinant Human Erythropoietin in Healthy Subjects Objective: To compare the pharmacokinetics, tolerance, and safety of subcutaneously administered single doses of two formulations of recombinant human erythropoietin (epoetin alfa, rhEPO) buffered with either phosphate or citrate and evaluate the significance of the buffer component in inducing pain.

Patients and Methods

Patients

Eighteen healthy volunteers ranged in age between 18–40 years of age (mean age 27 years) and weighed between 62.6–82.2 kg (mean weight 70.1 kg) were enrolled and completed this study. Subjects enrolled in the study had no clinically significant abnormal laboratory values for hematology or serum chemistry; had negative urine toxicology screen, HIV screen, and hepatitis B surface antigen. Subjects had no evidence of hypertension (e.g., diastolic blood pressure >95 mm Hg); had no history of any primary hematologic disease; history of significant hepatic, renal, cardiovascular, gastrointestinal, genitourinary, metabolic, or neurologic disease; had history of anemia or seizure disorder; a known sensitivity to mammalian-derived products or human serum albumin; had history of alcohol or drug abuse during the past two years; subjects were not habitual and heavy consumers to beverages containing caffeine; subjects had not participated in any other clinical trial or had blood transfused or donated within 30 days of study entry; subjects had not exposed to rhEPO within three months of study entry; subjects had no illness within seven days of study entry; and subjects had no significant abnormalities on the pre-study physical examination or the clinical laboratory evaluations within 14 days of study entry. All subjects were evaluable for safety and all blood collections for pharmacokinetic analysis were collected as scheduled. All studies were performed with institutional ethics committee approval and patient consent.

Study Design

This was a Phase I, single-center, open-label, randomized, two-period crossover study in healthy male volunteers. Eighteen subjects were randomly assigned to one of two treatment sequence groups (nine subjects/group). RhEPO was administered over two separate dosing periods as a bolus s.c. injection in the upper thigh. Each dosing period was separated by a 14-day washout period. Subjects were confined to the study center at least 12 hours prior to and 72 hours following dosing for each of the two dosing periods. The dosing regimen is summarized in Table 6.

TABLE 6

Dosage regimen and study design

| Group | N | Period 1 | Washout Period | Period 2 |
|---|---|---|---|---|
| I | 9 | Single dose of 150 IU/kg rhEPO s.c. with phosphate buffer | 14 days | Single dose of 150 IU/kg rhEPO s.c. with citrate buffer |
| II | 9 | Single dose of 150 IU/kg rhEPO s.c. with citrate buffer | 14 days | Single dose of 150 IU/kg rhEPO s.c. with phosphate buffer |

Two formulations of EPO were used in this study. Epoetin alfa (marketed as EPREX® 10,000 IU/mL) prepared in citrate buffer and a new formulation of rhEPO (10,000 IU/mL) prepared in phosphate buffer. Both formulations are manufactured by Ortho Biologics Division of Ortho McNeil Janssen Pharmaceuticals, Inc. (Manati, Puerto Rico).

Blood Sampling

Serial blood was drawn by direct venipuncture before and after administration of EPO; a heparin lock was not employed. Venous blood samples (5 mL) for determination of serum erythropoietin concentrations were obtained at ~30, 20, and 10 minutes prior to dosing (3 baseline samples) and at approximately the following times after dosing: 30 minutes and at 1, 2, 5, 8, 12, 15, 18, 24, 48, and 72 hours. Each serum sample was divided into two aliquots. All serum samples were stored at −20° C. Serum samples were shipped on dry ice. Fasting clinical laboratory tests (hematology, serum chemistry, and urinalysis) were performed immediately prior to the initial dose on Day 1, the morning of Day 2, immediately prior to dosing on Day 16, and the morning of Day 17.

Bioanalytical Methods

Sample analyses for serum erythropoietin levels were performed at RWJPRI. A radioimmunoassay (RIA) kit procedure (Diagnostic Systems Laboratory [DSL], Webster TX), was used for the determination of serum erythropoietin concentrations. The commercially available RIA is a double-antibody, competitive method that uses a rabbit polyclonal antiserum to human urinary erythropoietin as the primary antibody and $^{125}$I-labeled human urinary erythropoietin as the tracer. The DSL kit was modified by substitution of epoetin alfa for urinary erythropoietin in standards and quality control samples. Standard concentrations used in the assay were 7.8, 15.6, 31.25, 50, 62.5, 100, and 125 mIU/mL. Sensitivity, defined as the mean back-fit value for the lowest standard giving acceptable precision, was 8.6 mIU/mL, and the assay range was extended to 2,000 mIU/mL through quality control dilutions.

Safety Determinations

Vital signs were recorded immediately prior to each dosing (Days 1 and 16), and at 6, 24, 48, and 72 hours after each dosing. Safety determinations were based on the incidence and type of adverse events and the changes in clinical laboratory tests from baseline. In addition, changes from pre-study in vital sign measurements, including blood pressure, and physical examination results were evaluated.

Tolerance Determinations

Tests to assess the tolerance at the site of injection were administered 45 minutes after each injection on dosing days. There were two pain scales: a visual analog scale (VAS), consisting of a 10 cm horizontal line without gradations, and a verbal descriptive scale (VDS), consisting of five vertically placed boxes with adjacent descriptions. The end points of the VAS scale ranged from "no pain" to "the worst I can imagine", and those of the VDS scale ranged from "no pain" to "very severe pain". Additionally, the subjects were asked about the duration of pain.

Data Analysis

Post-dose serum concentration values were corrected for pre-dose baseline erythropoietin concentrations by subtracting from each of the post-dose values the mean baseline erythropoietin concentration determined from averaging the erythropoietin levels from the three samples collected at 30, 20, and 10 minutes before dosing. Pre-dose serum erythropoietin concentrations were not included in the calculation of the mean value if they were below the quantification level of the assay. Pharmacokinetic parameters were determined from serum concentration data corrected for baseline erythropoietin concentrations.

Pharmacokinetic parameters were calculated by model independent methods on a Digital Equipment Corporation VAX 8600 computer system using the BIOAVL software Version 8.0 (Scientific Computer Systems, RWJPRI). The following pharmacokinetic parameters were determined: peak serum concentration ($C_{max}$); time to peak serum concentration ($t_{max}$); area under the concentration-time curve (AUC) from time zero to the last blood sampling time ($AUC_{0-72}$) calculated with the use of the linear trapezoidal rule; and terminal elimination half-life ($t_{1/2}$), computed from 0.693/elimination rate constant. The elimination rate constant was estimated by linear regression of consecutive data points in the terminal linear region of the log-linear concentration-time plot. A minimum of three data points was used in the regression. For those regressions with coefficients of determination ($r^2$) <0.95, the corresponding $t_{1/2}$ values were not reported. The mean, standard deviation (SD), and coefficient of variation of the pharmacokinetic parameters were calculated for each treatment. The ratio of the mean pharmacokinetic parameters (phosphate/citrate) was calculated.

Statistical analysis was carried out on both raw and log-transformed bioavailability parameters. Analysis of variance models were fit to the data with one of the bioavailability parameters of interest (AUC, $C_{max}$—both raw or log-transformed) as the dependent variable and the effects due to treatment sequence group, subjects nested within the sequence groups, treatment and period as predictors. The test for the treatment sequence group effect was carried out at a 10% level of significance using the mean square due to the subjects nested within sequence groups as the error term. The period and treatment effects were tested at a 5% level of significance using the residual error term. The error mean square from the above model was used to estimate the intra-subject variability. Using the estimated intra-subject variability, the 90% confidence intervals were constructed for the ratio of the mean bioavailability parameters of rhEPO with phosphate buffer to rhEPO with citrate buffer.

Statistical analyses were performed on the three tolerance parameters. Before statistical testing could be performed, VAS scores and duration of pain values were transformed for normalization. All three parameters were analyzed by means of crossover test methods. The crossover analyses for the transformed VAS and duration of pain values were performed using Proc glm within SAS®. The study design was specified with a 14-day washout period to eliminate the possibility of carry-over between dosing periods. Thus, the calculations were based on the standard crossover model without carry-over effect. The results of pain assessed with the VDS were analyzed by means of the Wilcoxon-Mann-Whitney rank sum test, according to the methods on crossover trials described by Koch et al. In brief, this procedure consists of ranking the period differences for all of the patients in the trial and then using the Wilcoxon-Mann-Whitney test for differences between the two sequence groups.

Results

Safety Results

Six clinical adverse events (AEs) were reported by six subjects over both dosing periods: two AEs were reported in two subjects (11%) after receiving the citrate-buffered formulation and four AEs were reported in four subjects (22%) after receiving the phosphate-buffered formulation of the drug. The two AEs reported after injection of the citrate-buffered formulation were both within the respiratory system (i.e., pharyngitis and sinusitis). The four AEs reported after injection of the phosphate-buffered formulation included: muscle spasms, headache, leg pain, and dermatitis. All AEs from both groups were classified as mild and were transient in nature.

A decrease in total serum bilirubin concentrations was observed in all subjects the day following both injections for both formulations. The mean total bilirubin decreased to almost half the pre-dose baseline value over the two days of observation. However, the magnitude of this decrease was similar in both treatment groups, and mean total bilirubin levels remained within the normal range. This decline appeared to be transient, as the two pre-dose baseline values (16 days apart) were quite comparable. Similar changes in other liver function tests (alkaline phosphatase, SGOT, SGPT, LDH) were not observed.

Except for the unexpected decrease in total serum bilirubin, there were no clinically significant changes over the first two days following administration of the drug in physical examination, clinical laboratory tests, blood pressures, and vital sign measurements. Thus, the safety profiles for the two treatment groups appeared similar.

Tolerance Results

Two patients receiving the citrate-buffered formulation had missing pain recordings, one during each period. The mean VAS value of all 18 phosphate injections was 21.5±27.5 mm as compared to 34.3±28.6 mm of all 16 citrate injections (p=0.0692). Whereas sensation of pain after the phosphate solution was independent of the injections' period, the pain after the citrate formulation was sensed as more severe during period I than during period II (39.3±31.7 mm vs. 29.4±26.3 mm).

The difference between the two formulations in the VDS severity was statistically significant (p=0.0339). Thirteen subjects (72%) had either none or mild pain and five subjects (28%) had moderate/severe/very severe pain after the phosphate-buffered formulation. The corresponding recordings after the citrate-buffered formulation were made in 8 (44%) and 10 (56%) of the subjects, respectively. In addition, the VDS pain sensation was sensed as slightly more severe when the sequence was citrate/phosphate.

The duration of pain was significantly longer (p=0.0057) after the citrate-buffered formulation (1.5±2.0 minutes) than after the phosphate-buffered formulation (0.4±0.5 minutes). Whereas the difference was apparent already during period I (mean 0.8 vs. 0.3 minutes), it became quite evident during period II (mean 2.2 vs. 0.5 minutes), i.e., when the citrate receiving subjects already had experience with the phosphate solution. Of note, both drug formulations had one missing recording during period I. The present study has documented that the standard EPREX® formulation (with citrate) causes significantly more pain at the injection site than does the formulation using phosphate as the buffer. The sensation of citrate-induced pain was more intense when the sequence of testing was citrate/phosphate as opposed to phosphate/citrate, indicating that a baseline experience will modify the pain perception. Also concerning duration of pain, the difference between the two formulations was highly significant (p=0.0057), however, in this setting the citrate-induced pain was perceived much longer when the sequence was phosphate/citrate.

Pharmacokinetic Results

Figure 4:
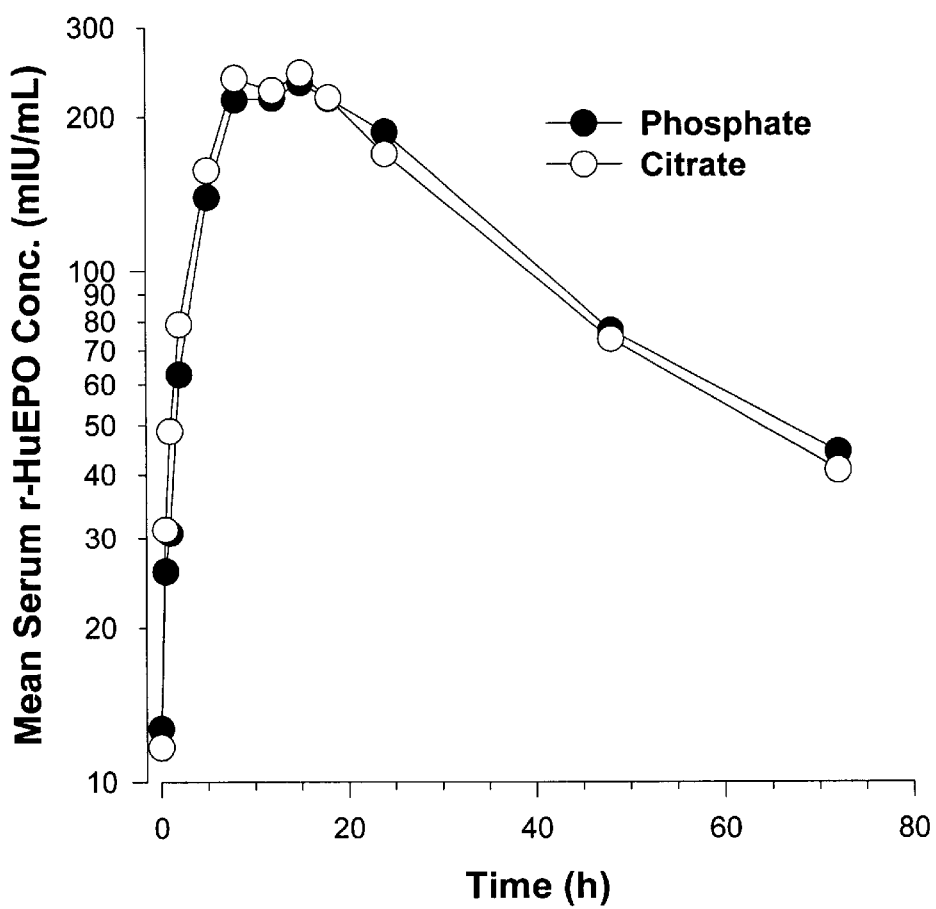
FIG. 4—Mean serum erythropoietin concentration-time profiles (uncorrected for baseline erythropoietin levels) for subjects receiving a single 150 IU/kg s.c. dose of rhEPO with citrate and phosphate buffer. Serum erythropoietin concentrations were determined by radioimmunoassay (RIA).

Mean serum erythropoietin concentration-time profiles (uncorrected for baseline erythropoietin levels) in all 18 subjects after receiving a single 150 IU/kg s.c. dose of rhEPO buffered in citrate or phosphate were similar (FIG. 4) All subjects had pre-dose baseline erythropoietin concentrations within the normal physiologic range (<8.6 to 18 mIU/mL).

Pharmacokinetic parameters were determined from serum data corrected for pre-dose mean baseline erythropoietin concentrations (Table 7). $C_{max}$ ranged from a low of 74 mIU/mL to a high of 583 mIU/mL (mean 260±169 mIU/mL) for rhEPO with citrate buffer and from 64 mIU/mL to a high of 642 mIU/mL (mean 245±167 mIU/mL) for rhEPO with phosphate buffer. A few subjects in each group had unusually high $C_{max}$ values. There was no statistically significant difference (p>0.05) in $C_{max}$ between the two formulations. For the rhEPO formulation with citrate buffer, the mean erythropoietin $AUC_{(0-72h)}$ was 7,992±3,319 mIU·h/mL, ranging from 3,215 to 13,077 mIU·h/mL. Similarly, the rhEPO formulation with phosphate buffer had a mean erythropoietin of $AUC_{(0-72h)}$ of 8,059±4,021 mIU·h/mL, ranging from 3,445 to 17,996 mIU·h/mL.(Table 7). There was no statistically significant difference (p>0.05) in $AUC_{(0-72h)}$ between the two formulations. The mean $t_{max}$ was similar for rhEPO with citrate and phosphate buffer (14±5 and 17±10 hr, respectively). The range for the $t_{max}$ was similar for both rhEPO formulations (8–24 hr). Mean terminal half-life values were similar for rhEPO with citrate and phosphate buffer (13.4±10.8 and 19.7±14.9 hr, respectively).

TABLE 7

Mean ± SD (% CV) pharmacokinetic parameters following a single 150 IU/kg s.c. dose of rhEPO with citrate and phosphate buffer

| Parameter | rhEPO without new stabilizer | rhEPO with new stabilizer | Ratio[a] | 90% Confidence Interval |
|---|---|---|---|---|
| $C_{max}$ (mIU/mL) | 245 ± 167 (68.1%) | 260 ± 159 (61.0%) | 0.94 | 73.3–115.2[b] 77.1–111.0[c] |
| $t_{max}$ (hr) | 17 ± 10 (57.7%) | 14 ± 5 (39.4%) | 1.21 | ND[d] |
| $AUC_{(0-72)}$ (mIU · h/mL) | 8.06 ± 4.02 (49.9%) | 7.99 ± 3.32 (41.5%) | 1.01 | 84.3–117.3[c] 87.0–112.4[d] |
| $t_{1/2}$ (hr) | 19.7 ± 14.9 (75.7%) | 13.4 ± 10.8 (80.5%) | 1.47 | ND |

[a]Parameter ratio, rhEPO with phosphate buffer/rhEPO with citrate buffer
[b]Raw data
[c]Log-transformed data
[d]Not Determined

REFERENCES

1. Koury S T, Bondurat M C, Koury M J. (1988) Localization of erythropoietin synthesizing cells in murine kidneys by in situ hybridization. Blood 71:524–527.
2. Jacobs K, Shoemaker C, Rudersdorf R, Neill S D, Kaufman R J, Mufson A, et al. (1985) Isolation and characterization of genomic and cDNA clones of human erythropoietin. Nature 313:806–810.
3. Lin F K, Suggs S, Lin C k, Browne J K, Smalling R, Egrie J C, et al. (1985) Cloning and expression of the human erythropoietin gene. Proc Natl Acad Sci USA 82:7580–7584.
4. Jelkmann W. (1992) Erythropoietin: structure, control of production, and function. Physiol Rev 72:449–489.
5. Egrie J C, Browne J K, Lai P, Lin F K. (1986) Characterization and biological effects of recombinant human erythropoietin. Immunobiology 172:213–224.
6. Faulds D, Sorkin E M. (1989) Epoetin (Recombinant Human Erythropoietin): A review of its pharmacodynamic and pharmacokinetic properties and therapeutic potential in anemia and the stimulation of erythropoiesis Drugs 38:863–899.
7. Markham A, Bryson H M. (1995) Epoetin alfa: A review of its pharmacodynamic and pharmacokinetic properties and therapeutic use in nonrenal applications Drugs 49:232–254.
8. Breymann C, Bauer C, Major A, et al. (1996) Optimal timing of repeated rh-erythropoietin administration improves its effectiveness in stimulating erythropoiesis in healthy volunteers. Brit J Heamatol 92:295–301.

9. Granolleras C, Leskopf W, Shaldon S, Fourcade J. (1991) Experience of pain after subcutaneous administration of different preparations of recombinant human erythropoietin: a randomized, double-blind crossover study. Clin Nephrol 36:294–298.

10. Frenken L A, Van Lier H J, Jordans J G, et al. (1993) Identification of the component part in an epoetin alfa preparation that causes pain after subcutaneous inject. Am J Kidney Dis 22:553–556.

11. Halstenson C E, Macres M, Katz S A, et al. (1991) Comparative pharmacokinetics and pharmacodynamics of epoetin alfa and epoetin beta. Clin Pharmacol Ther 50:702–712.

12. Ateshkadi A, Johnson C A, Oxton L L, Hammond T G, Bohenek W S, Zimmerman S W. (1993) Pharmacokinetics of intraperitoneal, intravenous, and subcutaneous recombinant human erythropoietin in patients on continuous ambulatory peritoneal dialysis. Am J Kidney Dis 21:635–642.

13. McMahon F G, Vargas R, Ryan M, et al. (1990). Pharmacokinetics and effects of recombinant human erythropoietin after intravenous and subcutaneous injections in healthy volunteers. Blood 76:1718–1722.

14. Salmonson T, Danielson B G, Wikstrom B. (1990) The pharmacokinetics of recombinant human erythropoietin after intravenous and subcutaneous administration to healthy subjects. Brit J din Pharmacol 29:709–713.

What is claimed is:

1. A pharmaceutical formulation of erythropoietin selected from the group consisting of:
    (a) a calcium chloride-free formulation comprising about 2000 IU erythropoietin, about 4.38 mg sodium chloride, 1.16 mg sodium phosphate monobasic dihydrate, 2.23 mg sodium phosphate dibasic dihydrate, about 5.00 mg glycine, about 0.30 mg Polysorbate 80, and adjusted to 1.0 mL with water;
    (b) a calcium chloride-free formulation comprising about 4000 IU erythropoietin, about 4.38 mg sodium chloride, 1.16 mg sodium phosphate monobasic dihydrate, 2.23 mg sodium phosphate dibasic dihydrate, about 5.00 mg glycine, about 0.30 mg Polysorbate 80, and adjusted to 1.0 mL with water;
    (c) a calcium chloride-free formulation comprising about 10,000 IU erythropoietin, about 4.38 mg sodium chloride, 1.16 mg sodium phosphate monobasic dihydrate, 2.23 mg sodium phosphate dibasic dihydrate, about 5.00 mg glycine, about 0.30 mg Polysorbate 80, and adjusted to 1.0 mL with water; and
    (d) a calcium chloride-free formulation comprising about 40,000 IU erythrdpoietin, about 4.38 mg sodium chloride, 1.16 mg sodium phosphate monobasic dihydrate, 2.23 mg sodium phosphate dibasic dihydrate, about 5.00 mg glycine, about 0.30 mg Polysorbate 80, and adjusted to 1.0 mL with water.

2. A pharmaceutical formulation of erythropoietin consisting essentially of:
    a) a pH buffering agent;
    b) a stabilizing amount of human serum albumin;
    c) a stabilizing amount of an amino acid;
    d) an antimicrobial quantity of cresol; and
    e) a pharmaceutical quantity of erythropoietin.

3. The formulation of claim 2 wherein the pH buffering agent is in a range of about 10 mM to about 30 mM.

4. The formulation of claim 3 wherein the pH buffering agent provides a pH range from about 5 to about 8.

5. The formulation of claim 4 wherein the pH buffering agent provides a pH range from about 6 to about 7.5.

6. The formulation of claim 5 wherein the pH buffering agent provides a pH of about 6.9.

7. The formulation of claim 2 wherein the pH buffering agent is selected from a group consisting of sodium phosphate monobasic/sodium phosphate dibasic, sodium citrate/citric acid, and sodium acetate/acetic acid.

8. The formulation of claim 7 wherein the pH buffering agent is in a range of about 10 mM to about 30 mM.

9. The formulation of claim 8 wherein the pH buffering agent provides a pH range from about 5 to about 8.

10. The formulation of claim 9 wherein the pH buffering agent provides a pH range from about 6 to about 7.5.

11. The formulation of claim 10 wherein the pH buffering agent provides a pH of about 6.9.

12. The formulation of claim 2 wherein the cresol preservative is meta-cresol in the range of about 0.2% to about 0.5% by weight/volume.

13. The formulation of claim 12 wherein the meta-cresol preservative is about 0.3% by weight/volume.

14. The formulation of claim 2 wherein the pharmaceutical quantity of erythropoietin is formulated to provide a Quantity per dose in the range of about 1000 IU to about 1 00,000 IU erythropoietin.

15. The formulation of claim 14 wherein the pH buffering agent is selected from a group consisting of sodium phosphate monobasic/sodium phosphate dibasic, sodium citrate/citric acid, and sodium acetate/acetic acid.

16. The formulation of claim 15 wherein the pH buffering agent is in a range of about 10 mM to about 30 mM.

17. The formulation of claim 16 wherein the pH buffering agent provides a pH range from about 5 to about 8.

18. The formulation of claim 17 wherein the formulation is provided as a multi-dose vial at a dose selected from the group consisting of about 10,000 IU/2.5 mL, about 25,000 IU/mL, and about 40,000 IU/2 mL.

19. The formulation of claim 2 wherein the stabilizing amount of albumin is 0.25 g/L.

20. The formulation of claim 2 wherein the amino acid is glycine.

21. The formulation of claim 20 wherein the stabilizing amount of glycine is in the range of about 5 g/L to about 50 g/L.

22. The formulation of claim 21 wherein the amino acid is glycine and is provided in the range of about 0.25 g/L to about 20 g/L.

23. The formulation of claim 22 wherein the pharmaceutical quantity of erythropoietin is formulated to provide a quantity per dose in the range of about 1000 IU to about 100,000 IU.

24. The formulation of claim 23 wherein the formulation is provided as a multi-dose vial at a dose selected from the group consisting of 10,000 IU/2.5 mL, about 25,000 IU/mL, and about 40,000 IU/2 mL.

25. The formulation of claim 20 wherein the glycine is about 5 g/L and wherein the stabilizing amount of albumin is about 0.25 g/L.

26. The formulation of claim 25 wherein the pharmaceutical quantity of erythropoietin is formulated to provide quantity per dose in the range of about 1000 IU to about 100,000 IU erythropoietin.

27. The formulation of claim 2 wherein said formulation is aqueous.

28. A pharmaceutical formulation of erythropoietin consisting essentially of:

a) a pH buffering agent;

b) a stabilizing amount of human serum albumin;

c) a stabilizing amount of an amino acid;

d) an antimicrobial quantity of cresol;

e) a pharmaceutical quantity of erythropoietin; and f) a tonicity agent.

29. The formulation of claim 28 wherein the pH buffering agent is in a range of about 10 mM to about 30 mM.

30. The formulation of claim 29 wherein the pH buffering agent provides a pH range from about 5 to about 8.

31. The formulation of claim 30 wherein the pH buffering agent provides a pH range from about 6 to about 7.5.

32. The formulation of claim 31 wherein the pH buffering agent provides a pH of about 6.9.

33. The formulation of claim 28 wherein the pH buffering agent is selected from the group consisting of sodium phosphate monobasic/sodium phosphate dibasic, sodium citrate/citric acid, and sodium acetate/acetic acid.

34. The formulation of claim 33 wherein the pH buffering agent is in a range of about 10 mM to about 30 mM.

35. The formulation of claim 34 wherein the pH buffering agent provides a pH range from about 5 to about 8.

36. The formulation of claim 35 wherein the pH buffering agent provides a pH range from about 6 to about 7.5.

37. The formulation of claim 36 wherein the pH buffering agent provides a pH range of about 6.9.

38. The formulation of claim 28 wherein the cresol preservative is meta-cresol in the range of about 0.2% to about 0.5% by weight/volume.

39. The formulation of claim 38 wherein the meta-cresol preservative is 0.3% by weight/volume.

40. The formulation of claim 28 wherein the pharmaceutical quantity of erythropoietin is formulated to provide a quantity per dose un the range of about 1000 IU to about 100,000 IU erythropoietin.

41. The formulation of claim 40 wherein the pH buffering agent is selected from a group consisting of sodium phosphate monobasic/sodium phosphate dibasic, sodium citrate/citric acid, and sodium acetate/acetic acid.

42. The formulation of claim 40 wherein the pH buffering agent is in a range of about 10 mM to about 30 mM.

43. The formulation of claim 42 wherein the pH buffering agent provides a pH range from about 5 to about 8.

44. The formulation of claim 43 wherein the formulation is provided as a multi-dose vial at a dose selected from the group consisting of about 10,000 IU/2.5 mL, about 25,000 IU/mL, and about 40,000 IU/2 mL.

45. The formulation of claim 28 wherein the stabilizing amount of albumin is about 0.25 g/L.

46. The formulation of claim 28 wherein the amino acid is glycine.

47. The formulation of claim 46 wherein the stabilizing amount of glycine is in the range of about 5 g/L to about 50 g/L.

48. The formulation of claim 49 wherein the amino acid is glycine and is provided in the range of about 0.25 g/L to about 25 g/L.

49. The formulation of claim 48 wherein the pharmaceutical quantity of erythropoietin is formulated to provide a quantity per dose in the range of about 1000 IU to about 100,000 IU.

50. The formulation of claim 49 wherein the formulation is provided as a multi-dose vial at a dose selected from the group consisting of about 10,000 IU/2.5 mL, about 25,000 IU/mL, and about 40,000 IU/2 mL.

51. The formulation of claim 28 wherein the tonicity agent is selected from a group consisting of sodium chloride, mannitol, glycine, glucose, and sorbitol.

52. The formulation of claim 46 wherein the glycine is about 5 g/L and wherein the stabilizing amount of albumin is about 0.25 g/L.

53. The formulation of claim 52 wherein the pharmaceutical quantity of erythropoietin is formulated to provide a quantity per dose in the range of about 1000 IU to about 100,000 IU erythropoietin.

54. The formulation of claim 28 wherein said formulation is aqueous.

55. A pharmaceutical formulation of erythropoietin selected from the group consisting of:

(a) about 10,000 IU erythyopoietin, about 6.25 mg human serum albumin, 2.91 mg sodium phosphate monobasic dihydrate, 11.19 mg sodium phosphate dibasic dodecahydrate, about 50.00 mg glycine, about 7.50 mg m-Cresol, adjusted to 2.5 mL with water;

(b) about 25,000 IU erythropoietin, about 6.25 mg human serum albumin, 2.91 mg sodium phosphate monobasic dihydrate, 11.19 mg sodium phosphate dibasic dodecahydrate, about 50.00 mg glycine, about 7.50 mg m-Cresol, adjusted to 2.5 mL with water; and (c) about 40,000 IU erythropoietin, about 5.00 mg human serum albumin, 2.33 mg sodium phosphate monobasic dihydrate, 8.95 mg sodium phosphate dibasic dodecahydrate, about 40.00 mg glycine, about 6.00 mg m-Cresol, adjusted to 2.0 mL with water.

* * * * *

UNITED STATES PATENT AND TRADEMARK OFFICE
CERTIFICATE OF CORRECTION

PATENT NO.      : 6,696,056 B1
DATED           : February 24, 2004
INVENTOR(S)     : Wing K. Cheung et al.

It is certified that error appears in the above-identified patent and that said Letters Patent is hereby corrected as shown below:

Title page,
Item [56], References Cited, OTHER PUBLICATIONS, "Breymann, Christian;" reference, please delete "292-301, and insert -- 295-301, -- therefor.
OTHER PUBLICATIONS, "Faulds, Diana;" reference, please delete "Eryhropoiesis." and insert -- Erythropoiesis. -- therefor.
"McMahon, Gilbert F.;" reference, after "Ramon;" insert -- Ryan, -- therefor.

Column 5,
Line 2, after "those" insert -- listed in Table A or Table B. -- therefor.

Column 6,
Line 66, please delete "maybe" and insert -- may be -- therefor.

Column 7,
Line 3, please delete "3,000 4,000" and insert -- 3,000, 4,000 -- therefor.

Column 12,
Line 4, please delete "Reconbinant" and insert -- Recombinant -- therefor.
Line 58, after "Study Design" start a new paragraph beginning with -- Both studies were phase I, single-center,......-- therefor.

Column 19,
Line 25, please delete "strengths." and insert -- strengths -- therefor.

Column 21,
Line 7, after "samples were stored in -20º C.", start a new paragraph beginning with "Serum samples were shipped…" therefor.

Column 25,
Line 27, please delete "din" and insert -- Clin -- therefor.
Line 51, please delete "erythrdpoietin," and insert -- erythropoietin, -- therefor.

Column 26,
Line 25, please delete "Quantity" and insert -- quantity -- therefor.
Lines 25-26, please delete "to about 1 00,000 IU" and insert -- to about 100,000 IU -- therefor.

UNITED STATES PATENT AND TRADEMARK OFFICE
CERTIFICATE OF CORRECTION

PATENT NO. : 6,696,056 B1
DATED : February 24, 2004
INVENTOR(S) : Wing K. Cheung et al.

It is certified that error appears in the above-identified patent and that said Letters Patent is hereby corrected as shown below:

Column 27,
Line 35, please delete "un" and insert -- in -- therefor.

Signed and Sealed this

Twenty-eighth Day of December, 2004

JON W. DUDAS
*Director of the United States Patent and Trademark Office*